(12) United States Patent
Fliri et al.

(10) Patent No.: US 10,242,091 B2
(45) Date of Patent: Mar. 26, 2019

(54) METHOD OF KNOWLEDGE EXTRACTION THROUGH DATA MINING

(71) Applicant: SystaMedic Inc., Groton, CT (US)

(72) Inventors: Anton F. Fliri, Stonington, CT (US); William T. Loging, Salem, CT (US); Robert A. Volkmann, Mystic, CT (US)

(73) Assignee: SYSTAMEDIC, INC., Stonington, CT (US)

( * ) Notice: Subject to any disclaimer, the term of this patent is extended or adjusted under 35 U.S.C. 154(b) by 342 days.

(21) Appl. No.: 15/022,808

(22) PCT Filed: Aug. 8, 2014

(86) PCT No.: PCT/US2014/050381
§ 371 (c)(1),
(2) Date: Mar. 17, 2016

(87) PCT Pub. No.: WO2015/021404
PCT Pub. Date: Feb. 12, 2015

(65) Prior Publication Data
US 2016/0259847 A1 Sep. 8, 2016

Related U.S. Application Data

(60) Provisional application No. 61/863,721, filed on Aug. 8, 2013.

(51) Int. Cl.
*G06F 17/30* (2006.01)
*G06Q 50/22* (2018.01)
(Continued)

(52) U.S. Cl.
CPC .. *G06F 17/30675* (2013.01); *G06F 17/30554* (2013.01); *G06F 17/30713* (2013.01);
(Continued)

(58) Field of Classification Search
CPC ......... G06F 17/30684; G06F 17/30598; G06F 17/2785; G06F 17/30424; G06F 17/30554;
(Continued)

(56) References Cited

U.S. PATENT DOCUMENTS 7,698,270 B2 * 4/2010 Brave ............... G06F 17/30867
707/603
8,462,160 B2 6/2013 Lindsay et al.
(Continued)

OTHER PUBLICATIONS

International Search Report and Written Opinion for application No. PCT/US2014/050381, dated Nov. 13, 2014, 10 pages.

*Primary Examiner* — Michelle N Owyang
(74) *Attorney, Agent, or Firm* — Ziegler IP Law Group, LLC

(57) ABSTRACT

The disclosed embodiments relate to data mining methods for determining economically valuable cause effect relationships between objects and properties associated with objects using co-occurrence frequency measurements of semantic terms characterizing observations of properties, effects or behaviors of objects in different environments and using these measurements as object descriptors in calculations determining object similarities. Specifically, these methods may be used to identify new indications of medicines, identify biomarkers associated with disease, identify biomarkers associated with drug effects, quantify disease diagnosis, identify novel drug targets, identify pharmacologic equivalencies of medicines, identify pharmacologic equivalencies between medicines and traditional medicines, identify pharmacologic equivalencies between medicines and Natural products, identify equivalencies between alternate medical procedures, identify risk benefit profiles of medicine combinations, identify targets for antibodies, identify synergies between medicines, identify Side effects of medi-
(Continued)

cines, identify risks of experimental medicines, identify functions of biological networks.

22 Claims, 5 Drawing Sheets

(51) Int. Cl.
*G06Q 10/06* (2012.01)
*G06F 19/00* (2018.01)
*G16H 50/30* (2018.01)
*G16H 50/70* (2018.01)

(52) U.S. Cl.
CPC ............ *G06F 19/00* (2013.01); *G06F 19/326* (2013.01); *G06Q 10/063* (2013.01); *G06Q 10/067* (2013.01); *G06Q 50/22* (2013.01); *G16H 50/30* (2018.01); *G16H 50/70* (2018.01)

(58) Field of Classification Search
CPC ......... G06F 17/30247; G06F 17/30675; G06F 17/30997; G06F 17/30616; G06F 17/30705; G06F 17/30861; G06F 17/30864; G06F 17/30713; G06F 17/30595; G06F 17/30696; G06F 17/30731; G06F 17/30489; G06F 17/30572; G06F 17/30734; G06F 17/2735; G06F 17/2795
USPC .................................................. 707/705–780
See application file for complete search history.

(56) References Cited

U.S. PATENT DOCUMENTS

| | | | |
|---|---|---|---|
| 8,478,699 B1* | 7/2013 | Alfonseca | G06F 17/3064 706/12 |
| 2005/0004790 A1 | 1/2005 | Wu et al. | |
| 2005/0154690 A1* | 7/2005 | Nitta | G06F 17/2217 706/46 |
| 2006/0259481 A1* | 11/2006 | Handley | G06F 17/2785 |
| 2007/0276857 A1* | 11/2007 | Fujio | G06F 17/30392 |
| 2008/0154992 A1 | 6/2008 | Lassalle | |
| 2010/0169327 A1 | 7/2010 | Lindsay et al. | |
| 2011/0087773 A1* | 4/2011 | Ishioka | G06F 17/30572 709/224 |
| 2013/0046723 A1* | 2/2013 | Sweeney | G06N 5/02 706/47 |
| 2013/0066823 A1* | 3/2013 | Sweeney | G06N 5/02 706/50 |
| 2013/0073571 A1 | 3/2013 | Coulet et al. | |
| 2013/0138665 A1* | 5/2013 | Hu | G06F 17/30731 707/749 |
| 2014/0214870 A1* | 7/2014 | Syeda-Mahmood | G06F 17/30386 707/758 |
| 2014/0280183 A1* | 9/2014 | Brown | G06F 17/30321 707/741 |
| 2014/0282586 A1* | 9/2014 | Shear | G06F 9/5072 718/104 |
| 2016/0103837 A1* | 4/2016 | Lee | G06F 17/3053 707/730 |

* cited by examiner

METHOD OF KNOWLEDGE EXTRACTION THROUGH DATA MINING

FIELD

The disclosed embodiments relate to data mining methods for determining economically valuable cause effect relationships between objects and properties associated with objects using co-occurrence frequency measurements of semantic terms characterizing observations of properties, effects or behaviors of objects in different environments and using these measurements as object descriptors in calculations determining object similarities. Specifically, these methods may be used to identify new indications of medicines, identify biomarkers associated with disease, identify biomarkers associated with drug effects, quantify disease diagnosis, identify novel drug targets, identify pharmacologic equivalencies of medicines, identify pharmacologic equivalencies between medicines and traditional medicines, identify pharmacologic equivalencies between medicines and Natural products, identify equivalencies between alternate medical procedures, identify risk benefit profiles of medicine combinations, identify targets for antibodies, identify synergies between medicines, identify side effects of medicines, identify risks of experimental medicines, and identify functions of biological networks.

BACKGROUND

A core aspect of knowledge is to apply observations of objects in different environments in the identification of relationships between the observed objects or properties associated with the observed objects and to use this understanding in the identification of cause effect relationships. With the amount of electronic information exponentially increasing, there is a growing need for extracting knowledge through data mining.

The extraction of knowledge through data mining requires identification of relationships among frequently large number of heterogeneous observations regarding attributes, characteristics, color, shape, virtues, merits, capacities, features, diagnostic fingerprints, properties, dependencies, actions, behavior, qualities, nearest neighbor interactions, functional relationships, functions, forces, purpose, effects that are associated with large numbers of objects often having very different units of measurements and scales (molecules, proteins, cells, tissues, organs, organisms, plants, animals, humans, planets, solar systems) and to discern amongst them observations that are meaningful for context recognition (the discernment of close relationships) from observations that are not meaningful for context recognition. [Rajaraman, A.; Ullman, J. D. (2011). "Data Mining". Mining of Massive Datasets. pp. 1-17.] Likewise the extraction of knowledge trough data mining also requires identification of objects sharing characteristic observation and the translation of this information into knowledge. In this respect, knowledge is a continuum ranging from the implicit end of the continuum such as statistical co-occurrences between objects and observations to more explicit knowledge such as causal relations.

Thus a first problem in knowledge extraction through data mining is addressed by the development of methods for the discernment of infrequent but meaningful observations from observations that are frequent but meaningless for context or group recognition. This is by no means an easy task and several methods have been developed for addressing this problem [(Yang, Guang-Zhong, and Magdi Yacoub. "Body sensor networks." (2006): 500); Robert Taaffe et al Displaying demographic information of members discussing topics in a forum U.S. Pat. No. 8,462,160)].

A second and more difficult problem in the extraction of knowledge through data mining is the identification of relationships between observations that have very different scales or unit of measurements (Fayyad, Usama, Gregory Piatetsky-Shapiro, and Padhraic Smyth. "From data mining to knowledge discovery in databases." *AI magazine* 17.3 (1996): 37.).

A third and even more difficult problem in extracting knowledge through data mining is the identification of cause effect linkage across disparate environments which require the quantification of similarities between observation having different unities of measurements and scales (Fliri, Anton F., William T. Loging, and Robert A. Volkmann. "Analysis of system structure-function relationships." *ChemMedChem* 2.12 (2007): 1774-1782).

A fourth problem arises with information gaps which are very common. To remedy this particular problem, methods have been explored for automatically inferring cause effect relationships. These approaches are usually divided into two main categories: proxy methods and natural language processing (NLP) based methods. Proxy methods attempt to use secondary observations associated with objects or events to infer cause effect relationships. For example, Burton and Simonitas used this approach for inferring cause effect relationships of medications using drug indication data. [Burton, M. M., Simonaitis, L., and Schadow, G. Medication and indication linkage: a practical therapy for the problem list?. *Proc AMIA Symp.* 2008; 86-90]. Lin and Haug described a more sophisticated system based on Bayesian networks [Lin, J. H. and Haug, P. J. Exploiting missing clinical data in Bayesian network modeling for predicting medical problems. *J Biomed Inform.* 2008; 41: 1-14]; Bayesian networks have the ability to model uncertainty arising with information gaps and analysis are based on a graphical formalism; wherein each variable is modeled as a node and causal relationship between two variables may be represented as a directed arc. For each node, a conditional probability table or formula is supplied that represents the probabilities of each value of this node, given the conditions of its parents. Application of this tool usually requires expert knowledge and training sets.

In addition to proxy methods, a variety of Natural Language Processing (NPL) methods have also been proposed. Such systems extract information from unstructured text such as clinical study progress notes and use association statistics for ascertaining cause effect relationships; however, one short coming of this approach is that NPL tools need customized dictionaries which limit the usefulness of NLP applications in broad text mining based cause effect analysis.

SUMMARY

Because an effect cannot precede its cause, we herein describe a method for determining cause-effect relationships between objects and object observations by using data mining tools for determining the co-occurrence frequencies between objects and semantic terms characterizing and identifying object observations, and entering the co-occurrence frequency information for object associated observations as descriptor sets in calculations for determining object similarities. Since co-occurrence frequencies are dimension less this methodology enables determination and examination of the transfer of cause effect linkage across environments with very different units and scale of measurements.

Hence these methods are particularly useful for examining the translation of effects of medicines, natural products and medicinal herbs on various cellular components into the generations of physiological effects in organisms.

The data mining technique relied on may erroneously be viewed as a method termed "frequent item sets and association rule mining". These particular data mining techniques have been developed in computer science for over a decade and have been used in a variety of fields. Frequent item sets, by themselves, are inherently non-directional which means that an item set (observation) is considered frequent if a count measuring the frequency of occurrence of a semantic term in a text document defining the item exceeds a certain threshold. However, some relationships between observation items have a direction because these observations are linked and hence the semantic terms associated with these observations co-occur more frequently than random chance would predict. One illustrative example frequently used is the very high co-occurrence frequency of the words insulin and diabetes in text document. This association frequency is caused by the fact that almost everyone who receives insulin has diabetes. Hence the key distinction between the method described herein and methods termed "frequent item set and association rule mining" is the use of statistics. In this regard the methods termed "frequent items set mining" and "association rule mining" use more or less sophisticated statistical methods for determining probability and confidence intervals that two co-occurring items (semantic terms) in a text document are associated.

In contrast, the method described herein does not determine the probability of associations between object observations but instead uses the co-occurrence frequencies between objects and semantic terms characterizing and identifying object observations as descriptor sets (fingerprints) of the observed objects. Association between observations are ascertained by determining similarities between objects and not by determining probabilities of observation term frequency analysis. This shift in focus from observation to objects allows the capturing of causal relationships between objects and objects observations. Using the example of the frequent co-occurrence of the semantic terms insulin and diabetes in text documents, the object focused method attributes the co-occurrence of the semantic terms insulin and diabetes to a diabetic patient's characteristic symptom pattern. Observation focused methods would instead use statistics for calculating the probability of the co-occurrence of the two semantic terms in patient records using term frequency analysis. [See for example Joshua Troche, Sebastian Crutch, and Jamie Reilly; Clustering, hierarchical organization, and the topography of abstract and concrete nouns; Front Psychol. 2014; 5:360].

Object focused methods often referred to as bag of word methods have been used in document classifications. These methods use a document-term matrix or term-document matrix which describes the frequency of terms that occur in a collection of documents. In a document-term matrix, rows correspond to documents in the collection and columns correspond to terms. One scheme for determining the value that each entry in the matrix has is the "term frequency—inverse document frequency" which is a numerical statistic that is intended to reflect how important a word is to a document in a collection or corpus. However these methods have not been used for extracting cause effect information through data mining.

Object focused analysis using frequent item sets as object descriptors has an advantage over observation focused analysis in cases where data are missing and incomplete which is particularly frequent in case of cause effect analysis involving biological systems. Using frequent terms of observations as object descriptors makes object similarity determination less vulnerable to missing data because determination of object similarity and concomitant association of observation depends on the entire descriptor set (fingerprint) and not on ascertaining probability of data point associations which may be partially missing. Hence the data mining based cause effect analysis method described herein is tolerant of absent or missing data. Moreover, contrasting the pleura of terms and synonyms describing observations, synonyms for object(s) are relatively easy to ascertain and can be used across a range of different databases.

BRIEF DESCRIPTION OF THE DRAWINGS

The present description will be better understood from the following detailed description read in light of the accompanying drawings, wherein.

DETAILED DESCRIPTION

Figure 1:
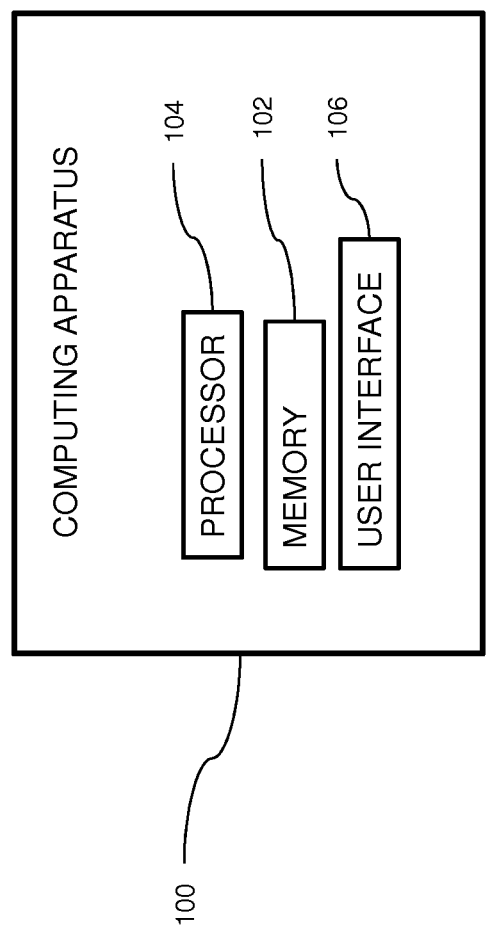
FIG. 1 shows a block diagram of a computing apparatus 100 that may be used to practice aspects of the disclosed embodiment.

In at least one aspect of the disclosed embodiments, the techniques disclosed herein may be executed by one or more computers under the control of one or more programs stored on computer readable medium. FIG. 1 shows a block diagram of an exemplary computing apparatus 100 that may be used to practice aspects of the disclosed embodiment. The apparatus 100 may include computer readable program code stored on at least one computer readable medium 102 for carrying out and executing the process steps described herein. The computer readable medium 102 may be a memory of the computing apparatus 100. In alternate aspects, the computer readable program code may be stored in a memory external to, or remote from, the apparatus 100. The memory may include magnetic media, semiconductor media, optical media, or any media which is readable and executable by a computer. Computing apparatus 100 may also include a computer processor 104 for executing the computer readable program code stored on the at least one computer readable medium 102. In at least one aspect, computing apparatus may include one or more input or output devices, generally referred to as a user interface 106 which may operate to allow input to the computing apparatus 100 or to provide output from the computing apparatus 100, respectively.

Figure 2:
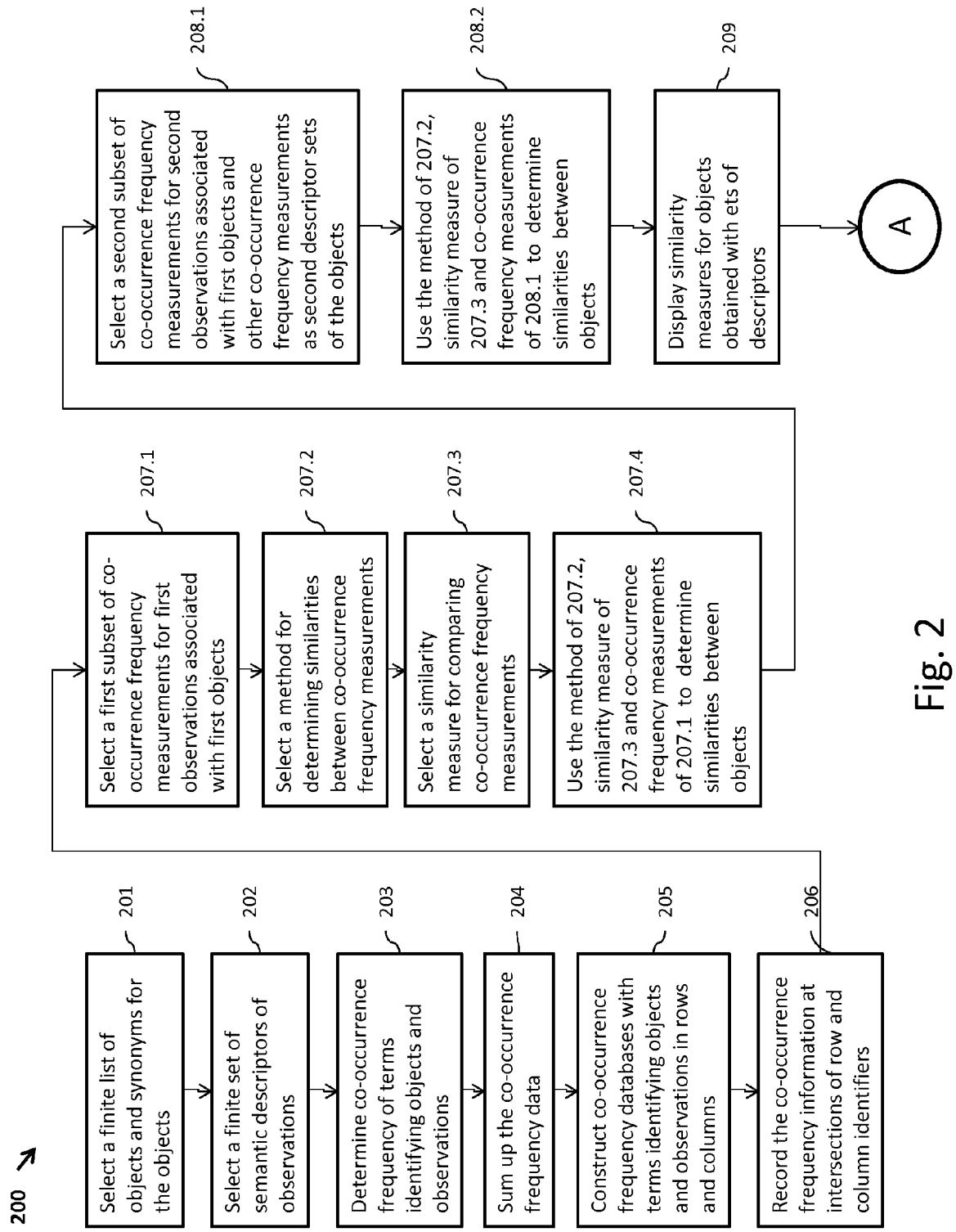
FIGS. 2 and 3 show a flow chart in accordance with the disclosed embodiments.
Figure 3:
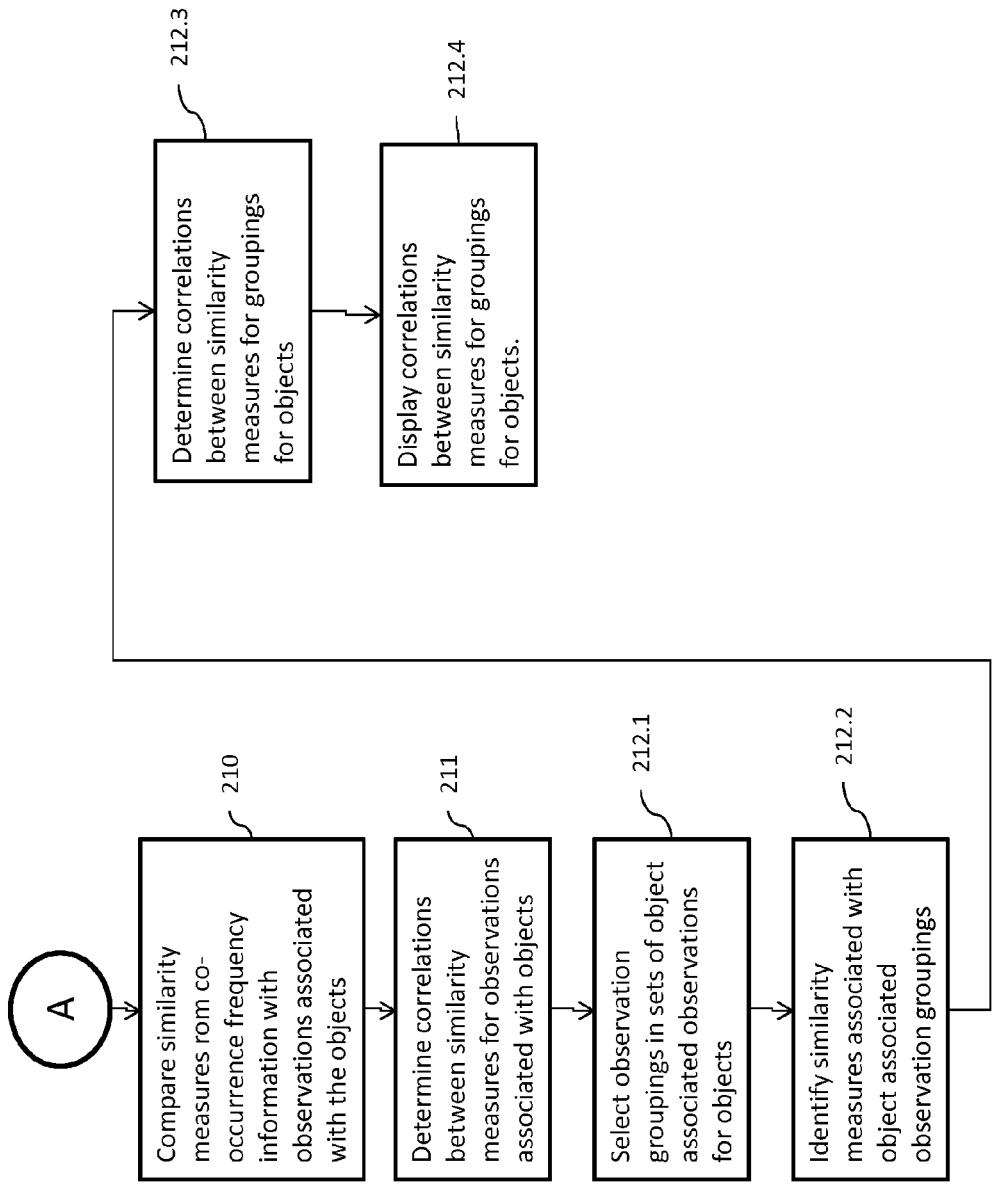

FIGS. 2 and 3 illustrate a data mining method 200 according to the disclosed embodiments. The computer processor 104 and the memory 102 including the computer readable program code are configured to cause the computing apparatus 100 to at least perform the data mining method disclosed herein. The data mining method 200 described herein comprises a first step 201 of selecting a finite list of objects and pertinent synonyms for each of the selected objects. In a second step 202, the selection of a finite set of semantic descriptors of observations characterizing and identifying effects, properties and behavior of objects in different environment said object observations selected from the group consisting of properties of matter, actions on composition of matter, activities, functions, behavior, modulation of behavior, qualities of composition of matter, interactions with biological systems, interaction with cellular components, effects on cellular components, pharmacological effects, toxicity, effects on ecological systems, effects on organ systems, effects on living organisms, effects on the environment, chemical structure, composition of matter, utility, economic value, manufacture, effects on disease, effects on social interactions, effects on information processing, societal effects, effects on commercial transactions, effects on information transmission, modulation of activities, modulation of functions, physicochemical properties, clinical utility, and therapeutic indications.

A third step 203 refers to the determination of the co-occurrence frequency of semantic terms identifying selected objects and the semantic terms identifying selected observations in at least one text containing data base.

A fourth step 204 refers to summing up of the co-occurrence frequency information obtained by using synonyms of selected objects in data mining.

Figure 4:
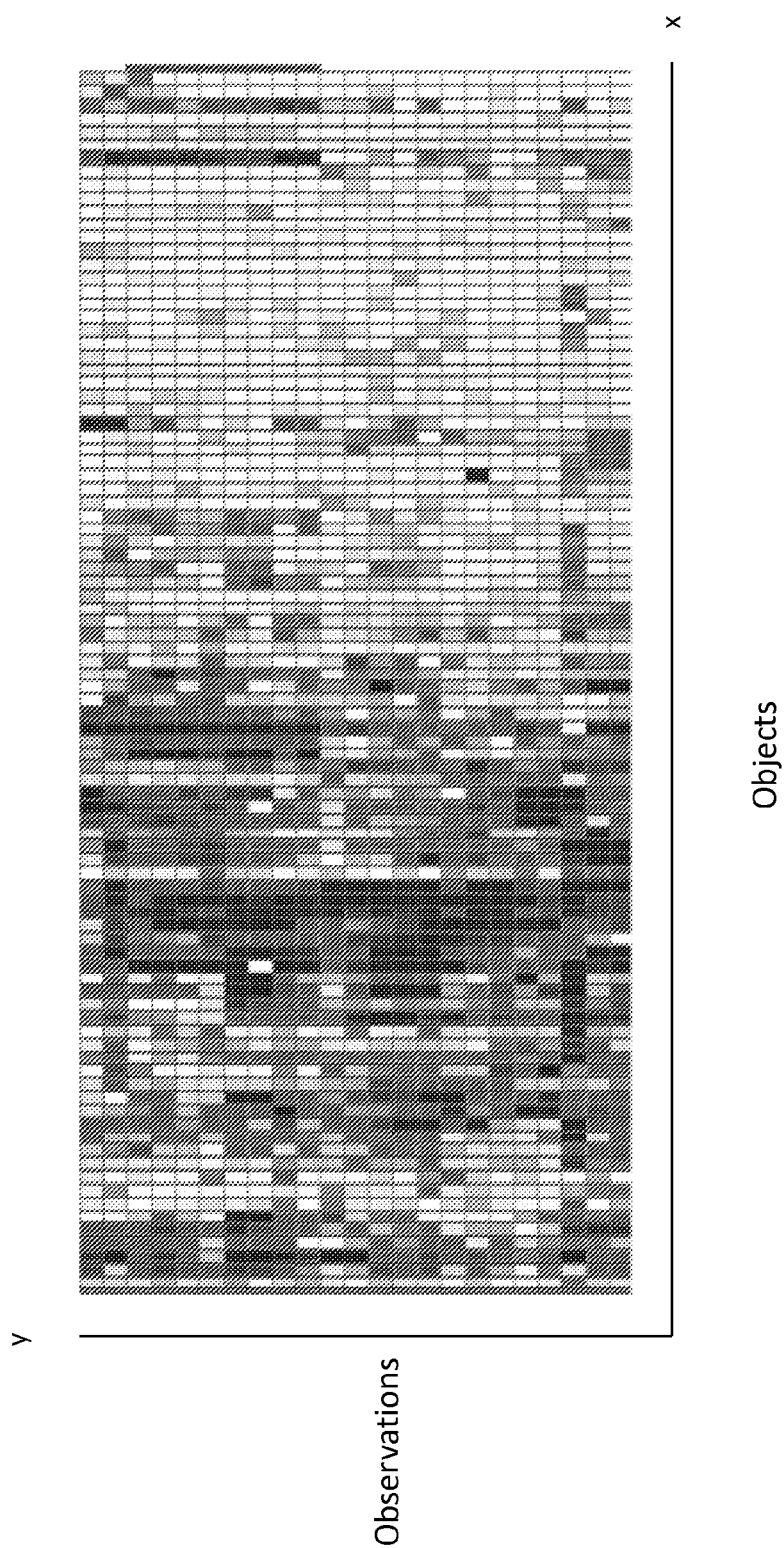
FIG. 4 shows a computer user interface display of exemplary similarity measures for various objects in accordance with the disclosed embodiments.
Figure 5:
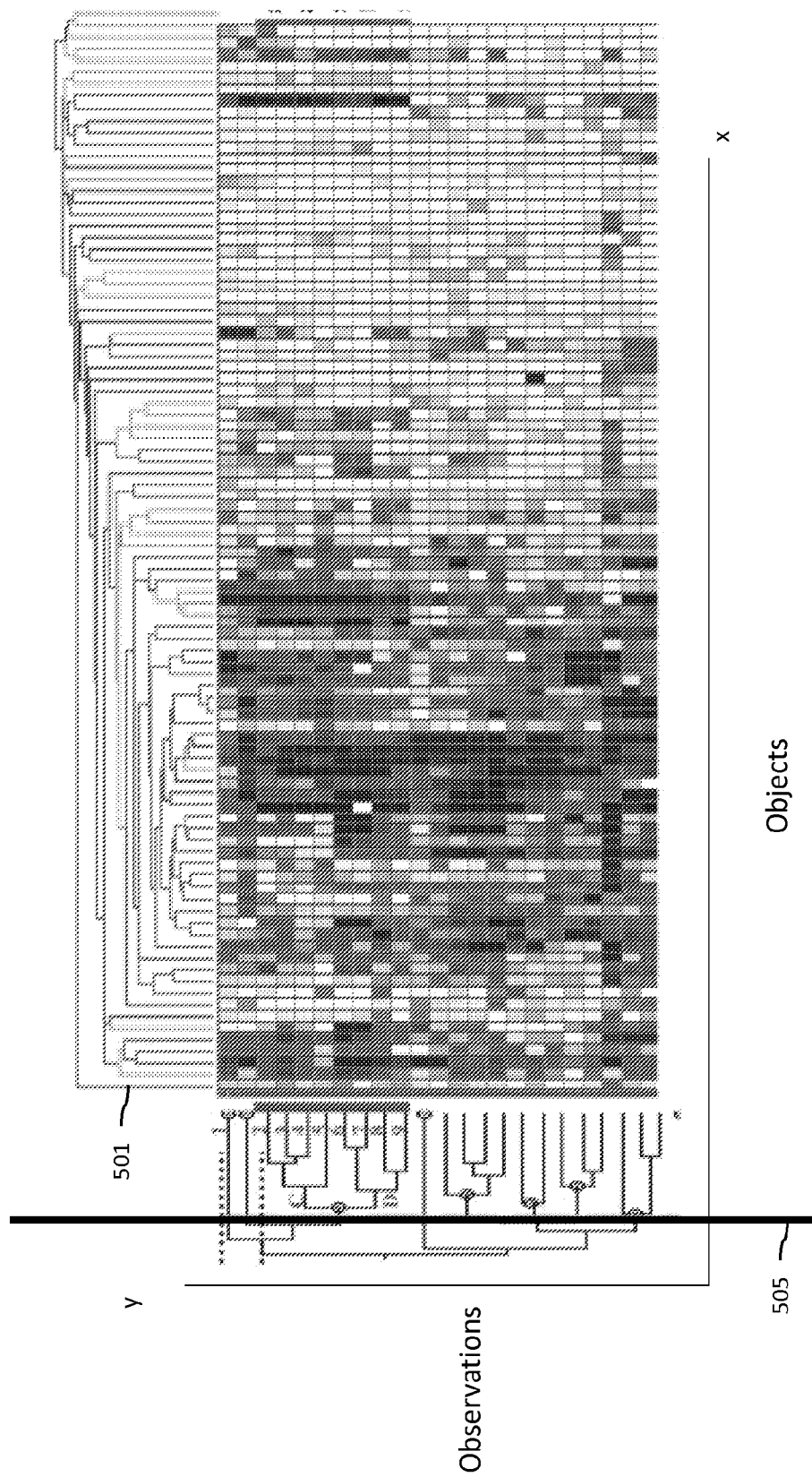
FIG. 5 shows a computer user interface display of correlations between the exemplary similarity measures for groupings for selected objects.

A fifth step 205 comprising the construction of co-occurrence frequency data bases wherein, the semantic terms identifying said objects are denoted either as rows or as columns in said databases providing either row or column identifiers in said database and wherein the semantic terms identifying said observations are either denoted as columns or as rows in said database providing either column or row identifiers in said data bases providing when objects are denoted as rows in said databases than said observations must be entered as columns in said data base or vice versa, A sixth step 206 comprising the recording of said co-occurrence frequency information at the intersections of said row identifiers with said columns identifiers in said data bases or each of the said selected objects and each of the said selected observations, A Seventh Step Comprising:

step 207.1 comprising the selection of a first subset of co-occurrence frequency measurements associated with a first set of observations associated with a first set of selected objects, a step 207.2 comprising the selection of a method for determining similarities between said co-occurrence frequency measurements associated with said objects and said observations, a step 207.3 comprising the selection of a similarity measure for comparing said co-occurrence frequency measurements associated with said objects, a step 207.4 comprising the use of the method selected in step (7.2) and the use of the similarity measure selected in step (7.3) and the use of said co-occurrence frequency measurements selected in step (7.1) in calculations determining similarities between said objects, An Eighth Step Comprising:

step 208.1 comprising the selection of co-occurrence frequency measurements associated with a second to nth set of observations associated with the first selected set of said objects and use of said other co-occurrence frequency measurements as second to nth descriptor sets of said selected objects, step 208.2) comprising the use of the method selected in step (7.2) and the use of the similarity measure selected in step (7.3) and the use of said co-occurrence frequency measurements selected in step (8.1) in calculations determining similarities between said objects, a ninth step 209 comprising the display of similarity measures for said objects obtained with said sets of said descriptors. FIG. 4 shows an exemplary illustration of the similarity measures presented on a display of user interface 106. The user interface display shows darker shades indicating more similarity and lighter shades indicating less similarity. While FIG. 4 shows Observations along the y-axis and Objects along the x-axis, it should be understood that Observations may be displayed along the x-axis and Objects along the y-axis.

tenth step 210 comprising the comparison of said similarity measures derived from co-occurrence frequency information associated with said sets of observations associated with said selected objects.

an eleventh step 211 for determining correlations between similarity measures for said sets of selected observations associated with said selected objects, A Twelfth Step step 212.1 comprising the selection of observation groupings in said sets of said object associated observation for selected objects step 212.2 the identification of similarity measures associated with said object associated observation groupings step 212.3 the determination of correlations between said similarity measures for said groupings for said selected objects Step (12.4) displaying the correlations between said similarity measures for said groupings for said selected objects. FIG. 5 shows an exemplary illustration of the correlations of the similarity measures presented on a display of user interface 106. Groupings are indicated by the lines outside the similarity indications. The length of the connectors 501 indicates relative correlation values. For example, connectors extending from the similarities indications beyond line 505 may have lower correlation values than those that do not extend beyond line 505. While FIG. 5 shows Observations along the y-axis and Objects along the x-axis, it should be understood that Observations may be displayed along the x-axis and Objects along the y-axis.

The finite list of objects includes pharmacologically active substances, medicines, diseases, plants, natural products of animal or plant origin, proteins, genes, in vivo assays, RNA, traditional medicines, drug combinations, food ingredients, merchandise, cosmetics, social network members and members of communities.

The finite list of observations includes effects of objects on: disease modification, disease outcome, modulation of disease symptoms, modulation of physiological effects and processes of in vivo models of disease, modulation of physiological effects in mammals, modulation of protein interactions, modulation of protein functions, modulation of cellular function, modulation of gene expression profiles, modulation of RNA expression profiles, modulation of protein expression profiles, modulation of gene expression profile, modulation of physiological processes, modulation of health, modulation of behavior, modulation of social interactions, modulation of network functions, modulation of network properties, substance associated properties, modulation of color, modulation of texture, modulation of taste perception, modulation of odor perception, modulation of morphology.

Methods for determining similarities between co-occurrence frequency information associated with object linked observations are known to those skilled in the art. One particular method is the hierarchical clustering method called UPGMA (Unweighted Pair Group Method with Arithmetic Mean). Likewise, similarity measures for comparing co-occurrence frequency information are known in the art and include for example the tool cosine correlation.

Methods for normalizing co-occurrence frequency information associated with object linked observations are known to those skilled in the art. One particular normalization method is based on determining the ratio of the frequency of the co-occurrence of a term associated with an object-observation and the base frequency of occurrence of the term in a database. Other ways of normalizing co-occurrence frequencies can be used as well.

Methods for visualizing object associated similarity measures are known to those skilled in the art. One particular method is the data visualization tool Spotfire. Other ways for visualizing similarity measures can be sued as well.

Methods for determining co-occurrence frequency information for object associated observations in data bases are known to those skilled in the art. One particular method is the Natural language Processing tool, MedLEE but other ways for obtaining co-occurrence frequency information can be used as well.

Any of the previous methods may be used for determining cause effect relationship of medicines. Any of the previous methods may be used for determining biological equivalence between prescription medicines and remedies used in traditional medicines or between prescription medicines and pharmacologically active substances isolated from animal or plant origin. Any of the previous methods can also be used for identifying new indications or side effects of medicines and new indications or side effects of combination of medicines. Any of the previous methods can also be used for identifying new indications or side effects of remedies used in traditional medicine. Any of the previous methods can also be used for identifying new indications or side effects of pharmacologically active substances isolated from animal, plant or microorganism origin. These methods can also be used for identifying biomarkers associated with disease. These methods can also be used for identifying biomarkers associated with drug effects. These methods can also be used for identifying effect biomarkers associated with administration of traditional medicines. These methods can also be used for identifying effect biomarkers associated with pharmacologically active substances isolated from animal, plant or microorganism origin These methods can also be used for the diagnosis of disease.

These methods can also be used for identifying novel drug targets.

These methods can also be used for identifying equivalencies between medical treatment protocols.

These methods can also be used for identifying molecular targets for antibodies.

These methods can also be used for identifying synergies between medicines.

These methods can also be used for identifying synergies between remedies used in traditional medicine and prescription medicines.

The invention claimed is:
1. A data mining method comprising:
   a first step comprising selecting, via a computer user interface, a list of objects and synonyms for each of the selected objects,
   a second step comprising selecting a first set of semantic descriptors of the selected objects and synonyms, and a second set of semantic descriptors of observations of the selected objects and synonyms,
   a third step comprising determining, using a computer processor, a co-occurrence frequency of the first semantic descriptors and the second semantic descriptors,
   a fourth step comprising summing up, using the computer processor, said co-occurrence frequencies of the first and second semantic descriptors,
   a fifth step comprising using the computer processor to construct co-occurrence frequency data bases, wherein the co-occurrence frequency data bases include row and column identifiers, and wherein the first set of semantic descriptors are denoted as row identifiers in said databases when the second set of semantic descriptors are denoted as column identifiers in said databases, and the first set of semantic descriptors are denoted as column identifiers in said databases when the second set of semantic descriptors are denoted as row identifiers in said data bases,
   a sixth step comprising recording, using the computer processor, said co-occurrence frequencies at intersections of said row identifiers and said columns identifiers in said data bases,
   a seventh step comprising:
      a step (7.1) comprising using the computer processor to select a first subset of co-occurrence frequency measurements associated with a first set of observations associated with a first set of the selected objects and synonyms,
      a step (7.2) comprising using the computer processor to select a method for determining similarities between said first subset of co-occurrence frequency measurements,
      a step (7.3) comprising using the computer processor to select a similarity measure for comparing said first subset of co-occurrence frequency measurements,
      a step (7.4) comprising causing the computer processor to use the method selected in step (7.2) and the similarity measure selected in step (7.3) and the co-occurrence frequency measurements selected in step (7.1) to determine first amounts of similarity between said first set of the selected objects and synonyms, an eighth step comprising:
      a step (8.1) comprising using the computer processor to select a second subset of co-occurrence frequency measurements associated with a second to nth set of observations associated with the first set of the selected objects and synonyms, and use of said second set of co-occurrence frequency measurements as second to nth descriptor sets of said selected objects,
      a step (8.2) comprising causing the computer processor to use the method selected in step (7.2) and the similarity measure selected in step (7.3) and the co-occurrence frequency measurements selected in step (8.1) to determine second amounts of similarities between said first set of the selected objects and synonyms,
   a ninth step comprising using the computer user interface to display the first and second similarity amounts for said first set of the selected objects and synonyms,
   a tenth step comprising using the computer processor to compare said first and second similarity amounts,
   an eleventh step comprising using the computer processor for determining correlations between the first and second similarity amounts, and a twelfth step comprising:
- a step (12.1) comprising using the computer processor to select observation groupings in said first set of the selected objects,
- a step (12.2) comprising using the computer processor to identify similarity amounts associated with said selected observation groupings,
- a step (12.3) comprising using the computer processor to determine correlations between said similarity amounts for said selected observation selected groupings; and
- a step (12.4) comprising using the computer user interface to display the correlations between said similarity amounts for said selected observation groupings.

2. A method of claim 1 wherein the list of objects is selected from the group consisting of diseases, plants, proteins, genes, effects, microorganism, medicinal herbs, herbal extracts, remedies used in traditional medicine, generally recognized as safe (GRAS) substances, in vivo assays, members of social network groups, business enterprises, members of communities.

3. A method of claim 1 wherein the list of objects comprises objects of composition of matter and the pertinent synonyms for each of the selected objects.

4. A method of claim 1 wherein the list of objects is selected from the group consisting of pharmacologically active substances, natural products, prescription medicines, generally recognized as safe (GRAS) substances, proteins, genes, and ribonucleic acid (RNA).

5. A method of claim 1 wherein the list of object associated observations is selected from the group consisting of semantic descriptors of properties of matter, actions on composition of matter, activities of composition of matter, functions of composition of matter, physical properties of composition of matter, physicochemical properties of composition of matter, chemical structure features of composition of matter, utilities of composition of matter, economic value of composition of matter, method of manufacture, interactions with biological systems, effects on behavior of organism, modulation of behavior of organisms, interaction with cellular components of organisms, effects on cellular components of organisms, pharmacological effects in organisms, effects on physical activities of organisms, modulation of organism functions, toxicity in mammals, effects on ecological systems, effects on organ systems, effects on living organisms, effects on the environment, effects on disease, effects on social interactions, effects on information processing, effects on society, effects on commercial transactions, effects on information transmission, effects on machines, clinical utility, therapeutic indications, economic value of social transactions, costs, selling price, price of manufacture, origin of manufacture.

6. A method of claim 1 wherein the list of observations is selected from the group consisting of disease symptoms, preclinical drug effect observations, effects in in vivo models of disease, clinical drug effects, modulation of protein interactions, modulation of protein functions, modulation of cellular function, modulation of gene expression profiles, modulation of RNA expression profiles, modulation of protein expression profiles, modulation of gene expression profiles, interactions with biological systems, effects on behavior of organism, modulation of behavior of organisms, interaction with cellular components of organisms, effects on cellular components of organisms, pharmacological effects in organisms, effects on physical activities of organisms, modulation of organism functions, toxicity in mammals, effects on organ systems.

7. A method of claim 1 wherein the method for determining similarities comprises an unweighted pair group method with arithmetic mean hierarchical clustering.

8. A method of claim 1 wherein the similarity measure is cosine correlation.

9. The use of the method of claim 1 for determining cause effect relationship of medicines.

10. The use of the method of claim 1 for determining new indications of medicines.

11. The use of the method of claim 1 for identifying biomarkers associated with disease.

12. The use of the method of claim 1 for identifying biomarkers associated with drug effects.

13. The use of the method of claim 1 for the diagnosis of disease.

14. The use of the method of claim 1 for identifying novel drug targets.

15. The use of the method of claim 1 for identifying pharmacologic equivalencies of medicines.

16. The use of the method of claim 1 for identifying pharmacologic equivalencies of medicines and traditional medicines.

17. The use of the method of claim 1 for identifying pharmacologic equivalencies of medicines and natural products.

18. The use of the method of claim 1 for identifying risk benefit profiles of medicine combinations.

19. The use of the method of claim 1 for identifying targets for antibodies.

20. The use of the method of claim 1 for identifying synergies between medicines.

21. The use of the method of claim 1 for identifying side effects of medicines.

22. The use of the method of claim 1 for identifying risks of experimental medicines.

* * * * *